(12) United States Patent
von Dyck et al.

(10) Patent No.: US 8,075,540 B2
(45) Date of Patent: Dec. 13, 2011

(54) BOWEL MANAGEMENT SYSTEM WITH PHYSIOLOGIC SENSORS

(75) Inventors: Peter M. von Dyck, Fernandina Beach, FL (US); John S. Minasi, Amelia Island, FL (US); James G. Schneider, Chesterfield, MO (US); Nick Martino, Fernandina Beach, FL (US)

(73) Assignee: Hollister Incorporated, Libertyville, IL (US)

( * ) Notice: Subject to any disclaimer, the term of this patent is extended or adjusted under 35 U.S.C. 154(b) by 1832 days.

(21) Appl. No.: 10/984,621

(22) Filed: Nov. 9, 2004

(65) Prior Publication Data
US 2006/0100595 A1   May 11, 2006

(51) Int. Cl.
 *A61F 5/44* (2006.01)
(52) U.S. Cl. .......................................... 604/348; 600/29
(58) Field of Classification Search .................. 604/317, 604/327, 346–348; 600/29, 31, 549; 607/41
See application file for complete search history.

(56) References Cited

U.S. PATENT DOCUMENTS

| 2,168,427 | A |   | 8/1939  | McConkey ................... 128/344 |
|-----------|---|---|---------|-------------------------------------|
| 4,176,660 | A |   | 12/1979 | Mylrea et al.                       |
| 4,263,921 | A | * | 4/1981  | Trugillo ........................ 600/549 |
| 4,304,239 | A |   | 12/1981 | Perlin                              |
| 4,413,633 | A |   | 11/1983 | Yanda                               |
| 4,459,841 | A |   | 7/1984  | Hok et al.                          |
| 4,497,324 | A |   | 2/1985  | Sullivan et al.                     |
| 4,637,814 | A |   | 1/1987  | Leiboff et al.                      |
| 4,671,296 | A |   | 6/1987  | Aitken                              |
| 4,809,710 | A |   | 3/1989  | Williamson                          |
| 5,009,662 | A |   | 4/1991  | Wallace et al.                      |
| 5,220,927 | A |   | 6/1993  | Astrahan et al.                     |
| 5,295,489 | A |   | 3/1994  | Bell et al.                         |
| 5,335,669 | A |   | 8/1994  | Tihon et al.                        |
| 5,368,565 | A |   | 11/1994 | DeLong                              |
| 5,370,671 | A | * | 12/1994 | Maurer et al. .................. 607/41 |
| 5,404,881 | A |   | 4/1995  | Cathaud et al.                      |
| 5,425,375 | A |   | 6/1995  | Chin et al. .................... 128/736 |
| 5,474,071 | A |   | 12/1995 | Chapelon et al. ........ 128/660.03  |
| 5,483,432 | A |   | 1/1996  | Wang                                |

(Continued)

FOREIGN PATENT DOCUMENTS

EP   0 282 449 A1   9/1988

(Continued)

OTHER PUBLICATIONS

European Examination Report for Application No. 05817559.7, dated Aug. 19, 2009.

(Continued)

*Primary Examiner* — Tatyana Zalukaeva
*Assistant Examiner* — Benedict L Hanrahan
(74) *Attorney, Agent, or Firm* — Marshall, Gerstein & Borun LLP

(57) ABSTRACT

A bowel management system includes a rectal catheter; and at least one physiologic sensor. The rectal catheter has a portion in contact with a patient's body internally thereof during use of the system, to thereby determine a preselected physiologic parameter of a patient having the rectal catheter inserted into the patient's bowel. The position of the sensor relative to the rectal catheter portion is such that the sensor is disposed in close proximity to the internal tissue of the patient, or within the fecal flow, when the bowel management system is place for use within the patient.

22 Claims, 4 Drawing Sheets

U.S. PATENT DOCUMENTS

| | | | |
|---|---|---|---|
| 5,569,216 A | 10/1996 | Kim et al. | |
| 5,704,353 A | 1/1998 | Kalb et al. | |
| 5,730,147 A | 3/1998 | Craig | |
| 5,792,070 A | 8/1998 | Kauphusman et al. | |
| 5,924,984 A * | 7/1999 | Rao | 600/373 |
| 6,010,511 A | 1/2000 | Murphy | |
| 6,033,366 A | 3/2000 | Brockway et al. | 600/486 |
| 6,056,699 A | 5/2000 | Sohn et al. | |
| 6,093,146 A | 7/2000 | Filangeri | |
| 6,120,457 A | 9/2000 | Coombes et al. | |
| 6,155,977 A | 12/2000 | Nowakowski | |
| 6,193,510 B1 | 2/2001 | Tsimerman | 433/29 |
| 6,296,615 B1 | 10/2001 | Brockway et al. | 600/486 |
| 6,334,064 B1 * | 12/2001 | Fiddian-Green | 600/311 |
| 6,348,039 B1 * | 2/2002 | Flachman et al. | 600/549 |
| 6,379,308 B1 | 4/2002 | Brockway et al. | 600/486 |
| 6,498,953 B2 | 12/2002 | Roe et al. | 607/41 |
| 6,536,260 B2 | 3/2003 | Williams | 73/40 |
| 6,595,930 B2 | 7/2003 | Rosenheimer | 600/561 |
| 6,616,597 B2 | 9/2003 | Schock et al. | 600/18 |
| 6,623,436 B2 | 9/2003 | Krivitski et al. | 600/505 |
| 6,625,495 B1 * | 9/2003 | Alon et al. | 607/116 |
| 6,663,570 B2 | 12/2003 | Mott et al. | 600/486 |
| 6,673,596 B1 | 1/2004 | Sayler et al. | |
| 6,677,859 B1 | 1/2004 | Bensen | |
| 6,679,906 B2 | 1/2004 | Hammack et al. | 607/105 |
| 6,699,186 B1 | 3/2004 | Wolinsky et al. | |
| 6,706,004 B2 | 3/2004 | Tearney et al. | |
| 6,723,040 B2 * | 4/2004 | Brady | 600/29 |
| 6,802,808 B2 | 10/2004 | Brady | |
| 6,843,766 B1 * | 1/2005 | Nemir et al. | 600/31 |
| 6,983,744 B2 | 1/2006 | Alfery | |
| 7,025,718 B2 | 4/2006 | Williams | |
| 7,087,026 B2 | 8/2006 | Callister et al. | |
| 7,147,627 B2 | 12/2006 | Kim et al. | |
| 7,186,222 B1 | 3/2007 | Callister et al. | |
| 7,381,190 B2 | 6/2008 | Sugrue et al. | |
| 2002/0019584 A1 | 2/2002 | Schulze et al. | |
| 2003/0035462 A1 | 2/2003 | Savoie | |
| 2004/0039348 A1 | 2/2004 | Kim et al. | |
| 2004/0100376 A1 | 5/2004 | Lye et al. | |
| 2005/0038380 A1 | 2/2005 | Nemir et al. | 604/66 |
| 2005/0222517 A1 | 10/2005 | Tiesma et al. | |
| 2005/0256447 A1 | 11/2005 | Richardson et al. | |
| 2005/0277805 A1 | 12/2005 | Hatton | 600/29 |
| 2006/0095032 A1 | 5/2006 | Jackson et al. | |
| 2006/0189951 A1 | 8/2006 | Kim et al. | |
| 2010/0234840 A1 | 9/2010 | Jackson et al. | |

FOREIGN PATENT DOCUMENTS

| | | |
|---|---|---|
| EP | 0282449 A | 9/1988 |
| WO | WO 2004/078071 A | 9/2004 |
| WO | WO-2004/078071 A1 | 9/2004 |

OTHER PUBLICATIONS

International Search Report from PCT/US2005/039738.

* cited by examiner

BOWEL MANAGEMENT SYSTEM WITH PHYSIOLOGIC SENSORS

CROSS-REFERENCE TO RELATED APPLICATIONS

None.

STATEMENT REGARDING FEDERALLY SPONSORED RESEARCH OR DEVELOPMENT

Not Applicable.

APPENDIX

Not Applicable.

BACKGROUND OF THE INVENTION

1. Field of the Invention

This invention relates generally to bowel management systems including rectal catheters, and, more particularly, to system wherein the rectal catheter has sensors embedded therein for physiologic monitoring/detection, screening of body state conditions such as temperature, oxygen saturation, infection, diseases, or other abnormalities, via interface with intestinal and intestinal contents whether solid, liquid or gas for example.

2. Related Art

Rectal thermometry and stool sampling are well known in the art of bowel management. However, current rectal thermometers require either repeated placement of a thermometer into the rectal vault for a short duration in order to get a temperature reading. Similarly, stool sampling techniques known in the art generally involve a messy process of either sampling stool that has been deposited by the patient in a receptacle such as a bed and bed pan or collection reservoir, or in some situations by physically removing stool from a patient. Both methods are unclean, messy, inexact, and unnecessarily expose the caregiver to the stool, which could contain hazardous infectious organisms and contaminated blood, and may also be extremely uncomfortable or hazardous for the patient.

There are many known catheter systems with physiologic sensing capability embedded in them for measuring pressure in the body and there are known rectal temperature probes. However, there are no known combination bowel management systems with both indwelling catheter portions and physiologic sensing capabilities.

The current devices to measure rectal temperature are inconsistent (due to uncontrolled placement of the temperature probe during each reading) and do not always gather an accurate measurement. None of these known rectally inserted probes can accurately interface with the anal canal. Other physiologic measurements such as oxygen saturation are usually done elsewhere on the body and while accurate, the methods include the caregiver managing additional equipment and may subject the patient to multiple tests. No known oxygen saturation monitors can simultaneously give measurements from the portal or mesenteric and the systemic circulations. Also, no known probes are for recording oxygen saturation from the portal or mesenteric circulation. Known stool sampling devices and methods are inconsistent, messy and subject the caregiver to unnecessary biological hazards.

The Bowel Management System (BMS) catheter which is used in patients to manage the output of stool resides atraumatically in the anorectum of the human and makes contact with the surrounding mucosa of the rectum and/or anal canal. This system is ideally of the basic type described in U.S. Ser. No. 10/225,820, pending, published Feb. 26, 2004, as Pub. No. US 2004/0039348A1, and owned by the assignee of the present invention, and the entire disclosure of which is incorporated herein by reference. Alternatively, the system of the present invention can include a rectal catheter (but without the cuff-shaped balloon-like bolster of FIG. 1), for example as of the type shown in FIG. 2, although not limited thereto. These locations of contact have proven to be preferred locations for sensing physiologic conditions such as temperature and oxygen saturation levels (experimentally). Dual sensors that measure portal or mesenteric (rectal) and systemic (anal canal) indices would have potential comparative values. Also due to the controlled passage of stool through the BMS, the BMS presents a more controlled way to sample the content of the stool when the stool is first exiting the anorectum for infections and blood content. Because the BMS resides in a patient's anal canal for up to about 29 days and has a portion that exits the anal canal within easy view of the caregiver, the BMS allows for placement of one or more physiologic sensors, in keeping with the present invention, in or attached to the indwelling portion of the catheter with corresponding readout device of the sensors outside the body of the patient by the caregiver.

Previously known devices to measure rectal temperature are inconsistent in performance (due to uncontrolled placement of the temperature probe during each reading) and do not always gather an accurate measurement. None of these known rectally inserted probes can accurately interface the anal canal. Other physiologic measurements such as oxygen saturation are usually done elsewhere on the body and while accurate, the methods include the caregiver managing additional equipment and possibly subjecting the patient to multiple tests. No known oxygen saturation monitors can simultaneously give measurements from the portal or mesenteric and the systemic circulations. Also, there are no known probes for recording oxygen saturation from the portal or mesenteric circulation. Known stool sampling devices and methods are messy and subject the caregiver to unnecessary hazards.

SUMMARY OF THE INVENTION

The BMS solution to sensing physiologic parameters solves many of the known problems in the art by having a portion of the catheter indwell in a patient's anorectum for up to about 29 days forming a close interface with the mucosa of the patient's rectum and the anal canal. Because the BMS stays fairly static during its indwelling duration a physiologic sensor either embedded within the internal portion of the balloon end of the device making contact with mucosa and fecal matter passing through the device or embedded within the external wall of the balloon end making contact with the mucosa and direct contact with fecal matter passing through the device or embedded within the proximal portion of the trans-sphincteric (anal canal) tube in contact with the anal canal of the patient allows the sensors to consistently and repeatedly make measurements from the same location within the patient. It is to be understood that by "embedded," throughout this document, it is meant that the sensor is at least partially buried or otherwise firmly secured to the tube, wall or other site at which it is disposed.

Because the BMS also has a portion that exits the anal canal and resides external of the patient, the sensors can be connected to a readout mechanism well external of the body allowing easy, controlled, uncontaminated reading of the sensor data by the caregiver. Similarly, sensors that sample the content of the stool passing through the BMS catheter overcome the messy, and often contaminated way of sampling stool by other devices and methods, by having the sampling tests built into sensors embedded within the balloon end of the catheter that sample the stool while it is initially passing through the catheter. This allows the caregiver to gather information such as blood content and other content information such as the presence of infection in the stool without handling the stool and sooner in the exiting of the stool before it is exposed to other environmental contaminants or has decay of critical content as is currently the practice.

Thus it will be appreciated that the new monitoring device can be made a part of both conventional and non-conventional rectal, anal canal and lower GI tract contents monitory systems. For example, monitoring systems as part of the present invention need not be limited to conventional temperature and oxygen saturation monitoring. Non-conventional monitoring systems when modified in accordance with the invention could include, but are not limited to, CO, carbon dioxide and lactic acid. Conventional lower GI tract monitoring need not be limited to clostridium difficile toxin, blood, lactoferrin and leukocyte esterase when modified in accordance with the present invention; and non-conventional monitoring could include, but need not be limited to, expressed indicators of physiologic or pathologic conditions, such as bowel ischemia, for example.

As will be made clear with reference to the figures the sensor indicator locations for the present invention may vary. In catheter configurations of the system the single sensor/indicator can be located in either the rectal or anal canal regions of the catheter. In dual sensor/indicator models located in the rectal and anal canal regions of the catheter there is allowance for measuring /monitoring/comparing differential values. For rectal locations, the sensors may be located internal to, external to, or embedded within the cuff inflation membrane. For rectal and/or anal canal locations the sensors maybe internal to, external to, or embedded within the wall which defines the catheter lumen; internal to, external to, or embedded within cuff or intralumenal balloon lumens; internal to, external to, or embedded within the irrigation/medication administration lumen; or internal to, external to, or embedded or otherwise placed within a dedicated sensor/indictor lumen.

Reactive indicators will react to contact with gas, liquid or solids testing positive for various pathologic conditions or physiologic states. Reactive indicator states include: Liquid, solid, mixture and suspension. The indicator can be introduced through the irrigation/medication administration lumen into the rectum or anal canal. When the indicator is introduced through a dedicated lumen, it can then pass into the rectum or anal canal or interact with effluent in a drain tube. The indicator may also be introduced into the catheter lumen via a reservoir or holding compartment. Further the indicator can be applied as a coating internal or external to the catheter lumen.

It is in view of the above problems that the present invention was developed. The invention is, briefly, a bowel management system including a rectal catheter; and at least one physiologic sensor. The rectal catheter has a portion in contact with a patient's body internally thereof during use of the system, to thereby determine a preselected physiologic parameter of a patient having the rectal catheter inserted into the patient's bowel. The position of the sensor relative to the rectal catheter portion is such that the sensor is disposed in close proximity to the internal tissue of the patient, or within the fecal flow, when the bowel management system is place for use within the patient.

The invention is further, briefly, the combination of an ano/rectal probe and an indwelling rectal catheter. The indwelling rectal catheter includes a drain catheter disposed during normal operative position within a portion of a patient's bowel, and the drain catheter has a wall defining a major lumen. The probe includes a sensor for detecting and transmitting information from the patent's bowel when disposed in close proximity to the mucosa of the rectum or anal canal of the patient, and an elongated portion connected to the sensor. The elongated portion is capable of conducting patient information from the sensor to a caregiver, and the probe is suitable for at least a single use and is sized and shaped so as to be insertable via a lumen of the catheter in order to gain access to a preselected monitoring site within the patient's bowel.

The invention is also, briefly, a method of managing a patient's bowel including the steps of:
  (a) providing a combination of an ano/rectal probe and an indwelling rectal catheter, the indwelling rectal catheter having a drain catheter;
  (b) positioning the drain catheter in a patient's bowel;
  (c) inserting the probe via a lumen of the drain catheter to a preselected monitoring site within the patient's bowel with a sensor of the ano/rectal probe disposed in close proximity to the mucosa of the rectum or anal canal of the patient for detecting and transmitting information from the patient's bowel; and
  (d) actively managing the patient's bowel, including selectively draining fecal material from the bowel, containing fecal material within the bowel until the time for selective draining and irrigating the patient's bowel.

Further features and advantages of the present invention, as well as the structure and operation of various embodiments of the present invention, are described in detail below with reference to the accompanying drawings.

BRIEF DESCRIPTION OF THE DRAWINGS

The accompanying drawings, which are incorporated in and form a part of the specification, illustrate the embodiments of the present invention and together with the description, serve to explain the principles of the invention. In the drawings.

Throughout the figures, like element numbers refer to like parts.

DETAILED DESCRIPTION OF THE PREFERRED EMBODIMENTS

Figure 1:
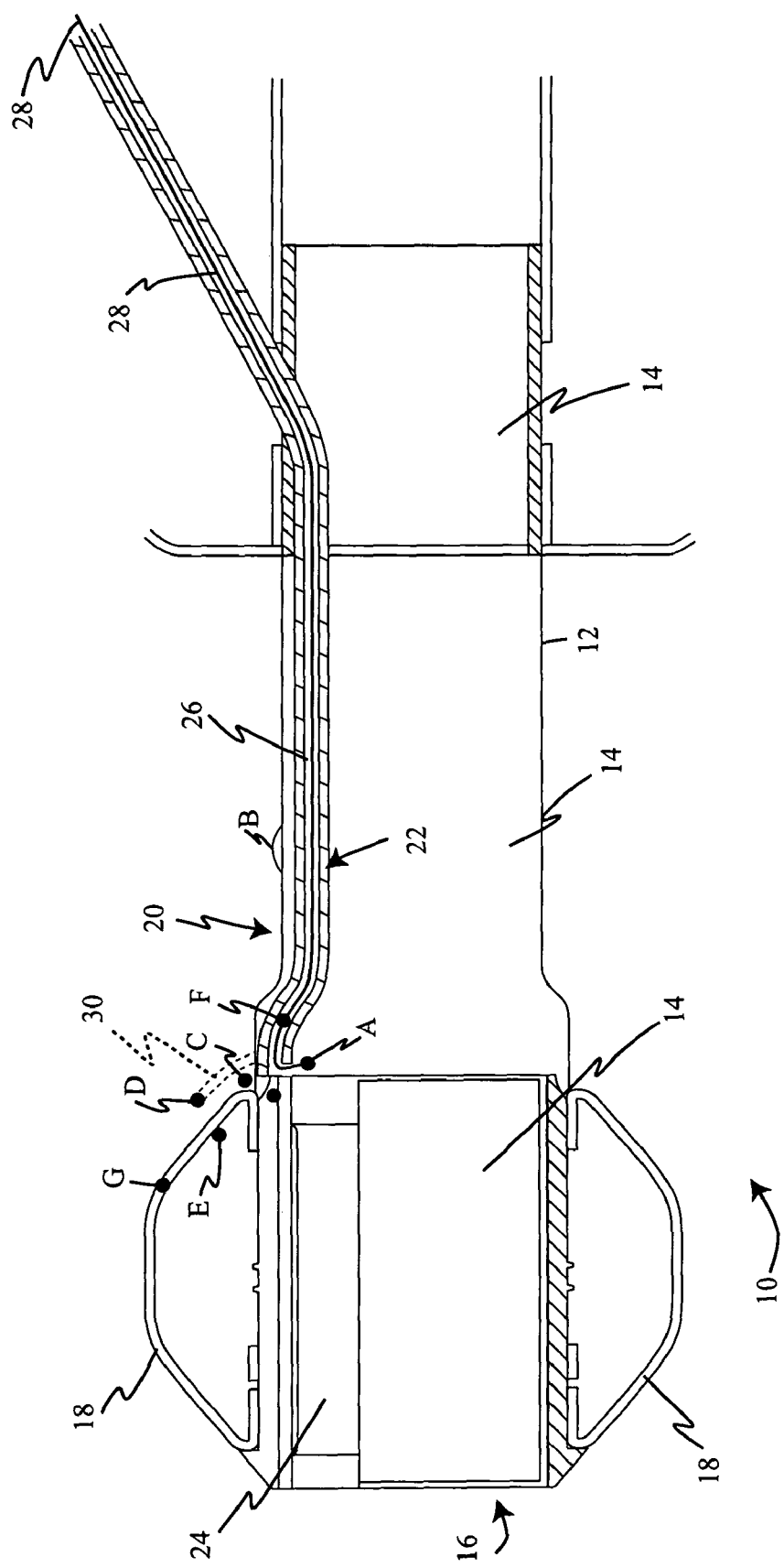
FIG. 1 is a longitudinal sectional side view of a rectal catheter having a bolster style retention mechanism and showing a physiologic sensor disposed at a variety of optional locations within or on the rectal catheter.

Referring to the accompanying drawings in which like reference numbers indicate like elements, FIG. 1 illustrates a bowel management system, generally designated 10, of a known type, except having physiologic sensors shown at a variety of useful locations within the system. System 10 includes a main catheter 12 defining a catheter drain lumen 14. The patient proximal end 16 of catheter 12 is surrounded by an annular balloon-like cuff 18, which serves as an inflatable bolster to retain the system in place for extended periods of time and to provide sealing with the rectal wall. Other suitable retention mechanisms may be satisfactorily substituted for bolster or cuff 18.

A variety of minor lumen can be part of system 10 by connection (usually, although not necessarily, longitudinally) on or within the catheter portion 14. A cuff inflation lumen 20 extends longitudinally along a central portion of main catheter 12 to provide a way to inflate and deflate cuff 18 as necessary. An intraluminal balloon inflation lumen 22 can extend longitudinally within drain lumen 14 to provide a way to inflate and deflate an optional anti-reflux valve 24 and an additional lumen 26 for introduction of medication or irrigation fluid can be disposed, for example, longitudinally between cuff inflation lumen 20 and anti reflux valve (ARV) inflation lumen 22. If desired, a sensor of the new invention can be provided with a transmission wire 28, which can be conveniently introduced via one of the lumen 20, 22, 26; the particular lumen depending upon the final site desired for the sensor. It is to be understood that the lumen, for the sensor wire may be dedicated entirely to the sensor, or may additionally be used for administration of medication or irrigation fluid, such as lumen 26, for example. Alternatively, the sensor may be of a nature which does not require a transmission wire; i.e. which is wireless, or which could occupy another, dedicated lumen, not shown.

Figure 3:
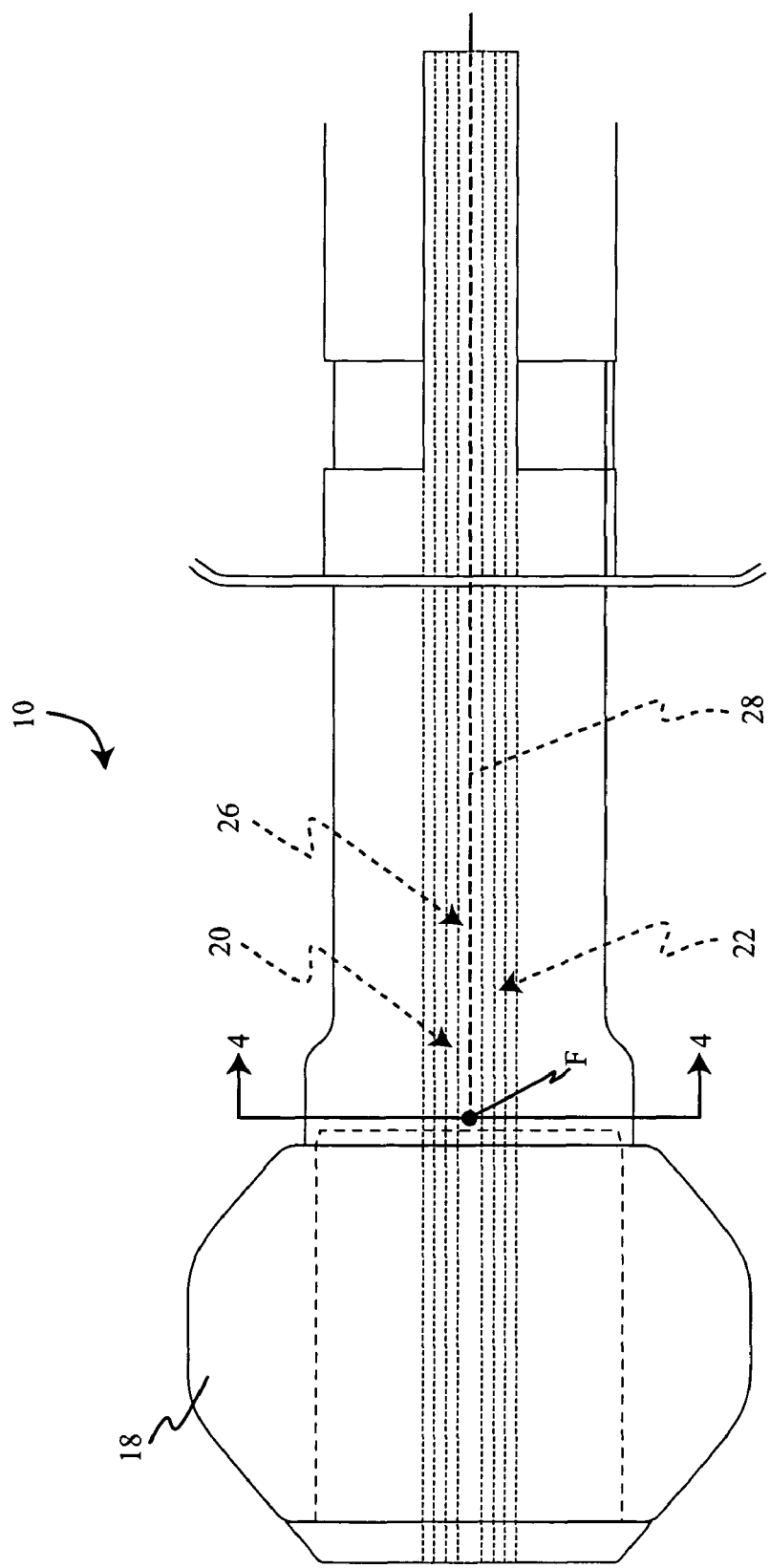
FIG. 3 is a longitudinal plan view, of the system of FIG. 1.
Figure 4:
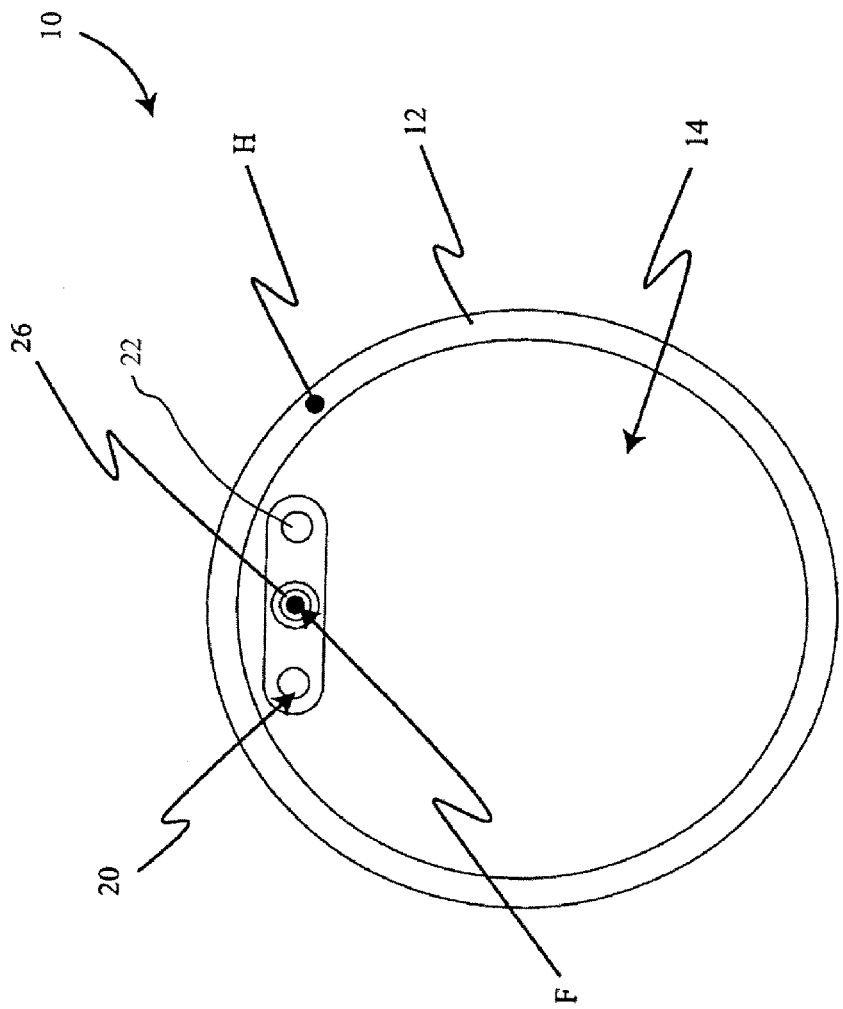
FIG. 4 is a transverse sectional view of the system of FIG. 1, taken on line 4-4 of FIG. 3.

FIG. 3 illustrates system 10 in top plan view with internal structures indicated in phantom. The sectional line 4-4 illustrates the site at which FIG. 4 is taken to better illustrate a practical disposition for the various lumens of system 10 and one possible position for sensor A.

With further reference to FIG. 1, it may be seen that one or more physiologic sensors, such as those indicated schematically at A-G, may be disposed at a variety of preselected positions within system 10. For example, as indicated in the figures by capital letters in the figures, as follows:

A. Internal to catheter lumen 14;
B. External to catheter lumen 14;
C. Internal to a dedicated cuff 30 (indicated in section, in phantom);
D. External to cuff 18
E. Internal to inflation cuff 18;
F. Embedded within a small lumen, such as within 26, for example; and/or
G. Embedded within cuff 18.
H. Embedded within the catheter wall (seen in FIG. 4 only).

Figure 2:
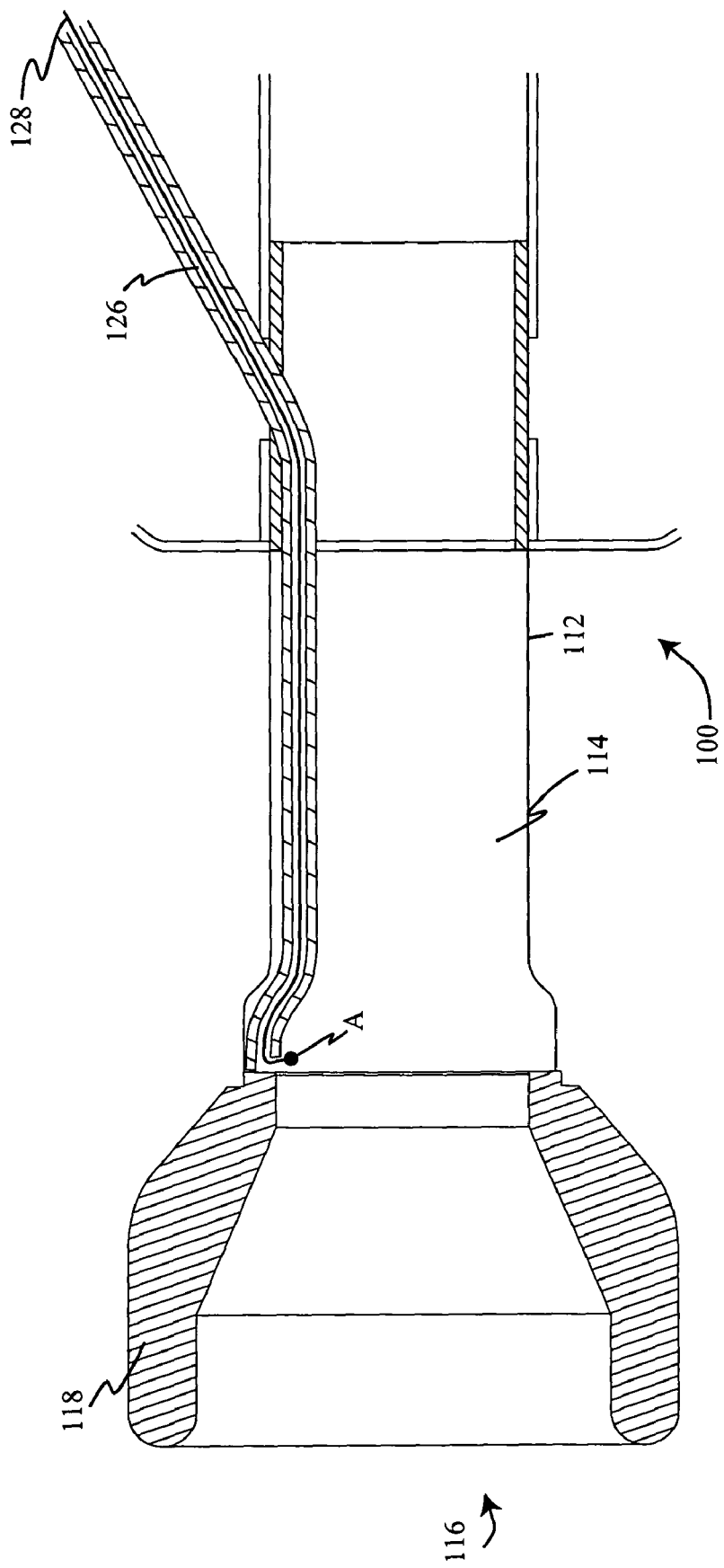
FIG. 2 is a longitudinal sectional view of a rectal catheter of an alternative style, also showing a physiologic sensor at a variety of optional locations within the catheter.

Similar pre-selected locations for the physiologic sensor can be utilized for the embodiment shown in FIG. 2, wherein 100 designates a bowel management system of an alternative embodiment, lacking an inflatable balloon-like cuff, but still including the new and unusual feature of physiologic sensor(s) disposed at preselected locations to facilitate accumulating of patient data. In this embodiment, system 100, like system 10, has a main catheter, here indicated at 112 and defining a lumen 114, which is of a size large enough for permitting drainage of the patient's bowel contents. A patient proximal end 116 of catheter 112 bears an inflatable balloon 118 into which a fluid can be introduced to expand it via a lumen 120. As in the first embodiment, the sensors can be operable via a transmission wire 128, or they can be of a suitable wireless type which is known or which may be developed.

In use the new system can accommodate a temporary sensor/probe whose placement is facilitated by the BMS catheter being in place. The probe can be a single use item or multiple use item that feeds through one of the lumens in the catheter in order to gain access to the monitoring site in close proximity to the internal tissue of the patient. Alternatively, the sensor can be placed more centrally within the catheter (not shown) so as to be located in the fecal flow from the patient. This position permits monitoring of the patient's excrement of any number of factors, such as pH level, chemical content, presence of particular pharmaceuticals, etc.

Alternatively, a probe or sensor may be built into a structure, such as a balloon, for example, that is built into the catheter. The probe can be periodically positioned for a reading or sampling by activating the structure (e.g., inflating the balloon).

The use of the invention can combine the two functions of active bowel management (fecal drainage, fecal containment, and irrigation and medication administration) and physiologic monitoring. Further, use of the new system permits combination of the functions of diagnostic and/or therapeutic administration and patient effluent monitoring.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. For example, other types of rectal catheters can be conceived that will also be suitable for use with the proposed physiologic sensors. Thus, the breadth and scope of the present invention should not be limited by any of the above-described exemplary embodiments, but should be defined only in accordance with the following claims appended hereto and their equivalents.

What is claimed is:

1. A bowel management system comprising:
a rectal catheter defining a catheter drain lumen, a portion of the rectal catheter configured to be disposed in contact with a patient's body internally thereof during use of the system, wherein the rectal catheter comprises a main catheter with a patient proximal end and a wall defining a major lumen, the patient proximal end being the portion configured to be disposed within the patient's bowel during use of the system and the major lumen providing communication between the interior of the patient's bowel and the exterior of the patient's body and having a size large enough for permitting drainage of the patient's bowel contents;
at least one physiologic sensor to thereby determine a preselected physiologic parameter of a patient having the rectal catheter inserted into the patient's bowel, wherein the position of each of the sensors relative to the rectal catheter portion is such that the sensor is disposed in close proximity to the internal tissue of the patient when the bowel management system is placed for use within the patient; and
a dedicated cuff at the patient proximal end of the main catheter, one of the at least one physiologic sensors being disposed one of internally of the dedicated cuff, externally on the dedicated cuff, or embedded within the material of which the dedicated cuff is formed.

2. The bowel management system of claim 1, and further comprising a wire connected to the at least one physiologic sensor and extending to outside of the patient's body in normal use position, to thereby transmit physiologic information from the patient to a caregiver.

3. The bowel management system of claim 1, wherein the at least one physiologic sensor is wireless.

4. The bowel management system of claim 1, wherein a second of the at least one physiologic sensors is disposed on the wall of the main catheter, externally to the catheter major lumen.

5. The bowel management system of claim 1, wherein a second of the at least one physiologic sensors is disposed internally on the wall of the main catheter, within the major lumen.

6. The bowel management system of claim 1, wherein a second of the at least one physiologic sensors is embedded within the catheter wall defining the major lumen.

7. The bowel management system of claim 1 and further comprising an inflatable cuff mounted to the patient proximal end of the main catheter to thereby retain the system within the patient's bowel when the inflatable cuff is inflated.

8. The bowel management system of claim 7, wherein a second of the at least one physiologic sensors is disposed internally of the inflatable cuff.

9. The bowel management system of claim 7, wherein a second of the at least one physiologic sensors is disposed externally of the inflatable cuff on an external surface thereof.

10. The bowel management system of claim 7, wherein a second of the at least one physiologic sensors is embedded within material of which the inflatable cuff is formed.

11. The bowel management system of claim 1 and further comprising at least one small diameter tube connected to the main catheter and having a wall defining a minor lumen.

12. The bowel management system of claim 11, wherein a second of the at least one physiologic sensors is disposed within the minor lumen.

13. The bowel management system of claim 11, wherein the at least one small diameter tube is connected inside the major lumen of the main catheter.

14. The bowel management system of claim 11, wherein one of the at least one physiologic sensors is embedded within the wall of a small diameter tube connected to the main catheter.

15. The bowel management system of claim 1, and further comprising a retention device mounted to the patient proximal end of the main catheter to thereby retain the system within the patient's bowel for extended periods of time.

16. The bowel management system of claim 15, wherein a second of the at least one physiologic sensors is disposed internally on the wall of the main catheter, within the lumen thereof.

17. The bowel management system of claim 15, wherein a second of the at least one physiologic sensors is disposed on the wall of the main catheter, externally to the main catheter lumen.

18. The bowel management system of claim 15, wherein a second of the at least one physiologic sensors is disposed internally of the retention device, substantially adjacent to the patient proximal end of the major lumen of the main catheter.

19. The bowel management system of claim 15, wherein a second of the at least one physiologic sensors is disposed externally of the retention device on an external surface thereof.

20. The bowel management system of claim 15, wherein a second of the at least one physiologic sensors is embedded within material of which the retention device is formed.

21. The bowel management system of claim 15, further comprising a dedicated cuff at the patient proximal end of the main catheter.

22. A bowel management system comprising:
a rectal catheter defining a catheter drain lumen insertable into a patient's bowel having a patient proximal end and a wall defining a major lumen, the patient proximal end being the portion configured to be disposed within the patient's bowel during use of the system and the major lumen providing communication between the interior of the patient's bowel and the exterior of the patient's body and having a size large enough for permitting drainage of the patient's bowel contents; and
at least one physiologic sensor within a portion of the rectal catheter; and
a dedicated cuff at a patient proximal end of the rectal catheter, one of the at least one physiologic sensors being disposed one of internally of the dedicated cuff, externally on the dedicated cuff, or embedded within the material of which the dedicated cuff is formed.

* * * * *